(12) United States Patent
Hurme et al.

(10) Patent No.: US 9,101,751 B2
(45) Date of Patent: Aug. 11, 2015

(54) METHOD AND SYSTEM FOR DISPLAYING THE ELECTRIC FIELD GENERATED ON THE BRAIN BY TRANSCRANIAL MAGNETIC STIMULATION

(75) Inventors: Raine Hurme, Helsinki (FI); Ilkka Autio, Espoo (FI); Perttu Sipilä, Helsinki (FI); Jarmo Ruohonen, Vantaa (FI)

(73) Assignee: Nexstim Oy, Helsinki (FI)

( * ) Notice: Subject to any disclaimer, the term of this patent is extended or adjusted under 35 U.S.C. 154(b) by 1798 days.

(21) Appl. No.: 11/853,232

(22) Filed: Sep. 11, 2007

(65) Prior Publication Data

US 2008/0161636 A1    Jul. 3, 2008

Related U.S. Application Data

(60) Provisional application No. 60/825,454, filed on Sep. 13, 2006.

(51) Int. Cl.
*A61N 2/02* (2006.01)
*A61N 2/00* (2006.01)
*G06T 17/20* (2006.01)
*G06T 19/00* (2011.01)

(52) U.S. Cl.
CPC ........ *A61N 2/006* (2013.01); *A61N 2/02* (2013.01); *G06T 17/20* (2013.01); *G06T 19/00* (2013.01); *A61N 2/004* (2013.01); *G06T 2210/41* (2013.01)

(58) Field of Classification Search
CPC ........... A61N 2/02; A61N 1/08; A61N 2/006; A61N 2/004; G06T 2207/30016
USPC ................................ 600/9–15, 407; 382/128
See application file for complete search history.

(56) References Cited

U.S. PATENT DOCUMENTS

| 6,849,040 B2 | 2/2005 | Ruohonen et al. ........ A61N 1/00 |
| 2004/0193002 A1 | 9/2004 | Tanner et al. |
| 2005/0113630 A1* | 5/2005 | Fox et al. ........................ 600/13 |

OTHER PUBLICATIONS

Ferrarelli, F. et al. "A [<17>F]-fluoromethane PET/TMS study of effective connectivity" Brain Research Bulletin, Elsevier Science Ltd., vol. 64, No. 2, Aug. 30, 2004, pp. 103-113.
Van'T Entvant Ent, et al. "A Fast Method to Dervice Realistic BEM Models for E/MEG Source Reconstruction" IEEE Transactions on Biomedical Engineering, IEEE Service Center, vol. 48, No. 12, Dec. 1, 2001.

(Continued)

*Primary Examiner* — Christine H Matthews
(74) *Attorney, Agent, or Firm* — Seppo Laine Oy (57) ABSTRACT

A visualization surface representative of a portion of the brain at a depth below the head surface of the subject is generated by combining an actual representation of the head surface with an idealized representation of the head surface. The combining is a function of the depth and is performed to minimize in the visualization surface any irregularities existing in the actual head surface of the subject. A display shows the visualization surface overlaid on a volumetric image of the brain, the electric field induced on a region of the visualization surface by a transcranial magnetic stimulation ("TMS") induction coil device positioned above the head surface and the TMS coil device. By viewing the display, a user of the TMS coil device can interactively position the TMS coil device in relation to the head surface and, for a target site on the brain at a selected depth, determine the position at which the TMS coil device induces a maximum E-field on a visualization surface corresponding to the selected depth.

21 Claims, 6 Drawing Sheets

(56) References Cited

OTHER PUBLICATIONS

Cuisenaire et al., "Registration and Real-Time Visualization of Transcranial Magnetic Stimulation With 3-D MR Images", IEEE Transactions on Biomedical Engineering, IEEE Service Center, vol. 51, No. 11, Nov. 1, 2004, pp. 1994-2005.
Herwig, "The Navigation of Transcranial Magnetic Stimulation", Psychiatry Research: Neuroimaging, vol. 108, No. 2, Nov. 30, 2001; pp. 123-131.
Ruohonen, "Background physics for magnetic stimulation", Jan. 1, 2003, pp. 3-12.
Ravazzani, P., et al., "Magnetic stimulation of the nervous system: induced electric field in unbounded, semi-infinite, spherical, and cylindrical media," Annals of Biomedical Engineering 24: 606-616, 1996.

\* cited by examiner

METHOD AND SYSTEM FOR DISPLAYING THE ELECTRIC FIELD GENERATED ON THE BRAIN BY TRANSCRANIAL MAGNETIC STIMULATION

CROSS REFERENCE TO RELATED APPLICATION

This application claims the benefit of U.S. Provisional Application No. 60/825,454 filed Sep. 13, 2006, assigned to the assignee of this application and incorporated by reference herein.

FIELD OF THE INVENTION

The present invention relates generally to transcranial magnetic stimulation and, more particularly, to displaying an accurate representation of the electric field induced on the brain of a subject by a transcranial magnetic stimulation induction coil device.

BACKGROUND OF THE INVENTION

Transcranial magnetic stimulation ("TMS") uses an induction coil in which a time-varying magnetic field is generated to induce an electric field ("E-field") within the brain. The neurons at the locations of the brain exposed to a strong enough E-field will become activated, or stimulated. In navigated brain stimulation ("NBS"), the E-field induced in the brain by a TMS induction coil device is shown as an overlay on a graphical display of an anatomical representation of the subject's brain. By viewing the display, a user can visualize the E-field induced on the brain and, therefore, interactively position the TMS coil device, in real time, in relation to the brain to stimulate a target site on the brain.

The following data acquisition and processing steps are typically performed as part of NBS.

1. A segmented data representation of the scalp or head surface of a subject is generated from data representative of the anatomical configuration of the subject's head. Typically, data representative of two-dimensional ("2D") magnetic resonance imaging ("MRI") images of the head of the subject, which was previously obtained using conventional MRI techniques, and where the images include at least the brain, upper parts of the skull and attached tissue and cartilage, are processed, using well known software algorithms, to generate a volumetric, three-dimensional ("3D") representation of the head. The 3D representation of the head is then further processed, also using well known software algorithms, to generate a segmented data representation of the head surface of the subject.

2. Tracking elements are implemented to provide that the location and orientation of a TMS coil device with respect to a subject's head can be tracked. As conventional in the art, easily identifiable, reflective markers (trackers) are placed on selected points on the subject's head and also the TMS coil device to permit automatic recording of the coordinates of the points in 3D and six degrees of freedom. For example, the trackers on the TMS coil device may be a part of a tracking device attached to the TMS coil device, as described in U.S. patent application for TRANSCRANIAL MAGNETIC STIMULATION INDUCTION COIL DEVICE WITH ATTACHMENT PORTION FOR RECEIVING TRACKING DEVICE, Ser. No. 11/847,544 filed Aug. 30, 2007, assigned to the assignee of this application and incorporated by reference herein, and the coordinates of the trackers are recorded using a special-purpose camera, as conventional in the art.

3. A co-registration procedure is performed, which correlates data representative of the coordinates of the trackers on the TMS coil device and the subject's head (2. above) with the image data from which the 3D representation of the subject's head is generated (1. above). Typically, several landmark points on the head, such as points on each ear and the nose, are pinpointed from the 2D MRI images or, if available, the volumetric 3D image of the head. The same points are also pinpointed on the subject's head by use of a digitization pen tracker. After performing such point-to-point correspondences or point-to-point matching, a transformation is computed that aligns the coordinate system of the MRI images of the head with the coordinate system of the trackers. The quality of the transformation can be enhanced, for example, at least in the least-squares sense, by performing additional point-to-point matching, which in turn improves the accuracy of NBS.

4. On a display typically used in NBS, a graphical representation of the TMS coil device, in particular preferably only the casing of the TMS coil device in which the coil windings are contained, is shown in relation to a graphical representation of the scalp and a portion of the brain at a selected depth, and the E-field induced on the brain portion by the TMS coil device is shown as an overlay on the brain portion. The display provides a user with a visual representation of the position and orientation of the casing, and thus the coil windings, of the TMS coil device in relation to the head and the brain, and also the E-field induced in the brain, as the user navigates the TMS coil device in relation to the subject's head. The quality of the transformation computed in the co-registration (3. above) affects the accuracy of the representations shown on the display and, thus, the navigation accuracy. As well known in the art, the E-field induced by the coil windings is computed using a head shape model, e.g., a spherical model, such as described in Ravazzani, P., et al., "Magnetic stimulation of the nervous system: induced electric field in unbounded, semi-infinite, spherical, and cylindrical media," *Annals of Biomedical Engineering* 24: 606-616, 1996, incorporated by reference herein, and based on a model of the shape and location of the copper windings inside the casing of the TMS coil device. The E-field is then shown on the representation of the brain portion, for example, using colors to indicate E-field strength, to provide that the user can navigate the TMS coil device to stimulate target sites on the brain portion. The accuracy of the representation of the brain portion, in a large part, determines the accuracy of the representation of the E-field induced on the brain portion shown on the display and, thus, greatly impacts the accuracy with which the user can navigate the TMS coil device to stimulate target sites on the brain.

It is known that the effects of TMS depend on both the absolute strength of the E-field at a target site on the brain and the relative strength of the E-field with respect to regions neighboring the target site. Consequently, it is important that the NBS display accurately show to the user of a TMS coil device the location of the maximum E-field in a neighborhood of interest for a target site. For anatomical reasons, the relevant neighborhoods of interest on a brain portion of a selected depth usually are represented on a prior art NBS display as surfaces oriented approximately parallel to the portion of the subject's scalp above the neighborhoods. Hence, in prior art NBS, the brain has been represented using a plurality of so-called visualization surfaces, each of which represents a portion of the brain at a selected depth.

In the prior art, an NBS display usually shows a visualization surface at a depth of about 20 to 25 mm beneath the scalp. The visualization surface approximates the shape of the brain and the cortical brain structures at the selected depth. In addition, the NBS display shows the E-field induced at points along the visualization surface, including the location of the maximum E-field on the visualization surface. The E-field ordinarily is shown as a colored map, where the coloration indicates strength relative to a maximum. In addition, the NBS display typically shows the TMS coil device in color in relation to the visualization surface. In addition, the visualization surface is also shown using colored and textured surfaces of polygons that are updated in real time, for example, as the TMS coil device or the head moves. Further, the prior art NBS display provides that the TMS coil device and the visualization surfaces may be viewed from any angle and distance.

In prior art NBS, a visualization surface is derived directly from the 2D MRI image data of the head, such that any protrusions (bumps), concavities or other irregularities in the scalp are correspondingly, substantially identically reflected in the visualization surface. Ideally, it is expected that the location of the maximum E-field would move along the visualization surface on an NBS display in correspondence with the movement of the TMS coil device along the scalp.

It is has been observed, however, on prior art NBS displays showing visualization surfaces, which have significant bumps, protrusions or irregularities, in relation to a TMS coil device and the E-field induced by the TMS coil device, that when the TMS coil device is moved gradually along the scalp of a subject, the representation of the E-field on the visualization surface becomes irregular and does not directly correspond to the movement of the TMS coil device along the scalp. For example, if a stimulation target site is at the bottom of a surface concavity on the visualization surface, the strength of the E-field at the target site displayed on the visualization surface is significantly weaker than that at points surrounding the target site, even though the actual strength of the E-field at the target site may be the same or about the same as the strength of the E-field at the surrounding points. It is well known in the art that the E-field induced by a TMS coil device weakens quickly with distance from the coil windings within the TMS coil device, and for example may weaken even about 5-20% at a distance of about 2 mm from the coil windings. Therefore, if a visualization surface closely approximates the shape of the scalp, the maximum E-field likely will not be shown as being located in a concavity in the visualization surface which constitute a stimulation target site and, instead, will be shown as being located at points on the visualization surface neighboring the target site and bordering the concavity. Consequently, where the visualization surface includes concavities that correspond to target sites, it is very difficult, if not impossible, to position the TMS coil device so that the maximum E-field is located at the target site on the visualization surface.

Alternatively, if a visualization surface does not closely approximate the shape of the brain, then the regions neighboring a target site likely will not be properly oriented, such that the objective of using NBS to accurately position the TMS coil device in relation to the head, so as to induce a maximum E-field at a target site, becomes unattainable.

Therefore, there exists a need for generating a visualization surface representative of a portion of the brain at a selected depth, for use in displaying the E-field induced on the brain by a TMS coil device as part of NBS, which accurately represents the brain portion at the selected depth and avoids erroneous representations of the E-field on the visualization surface.

SUMMARY OF THE INVENTION

In accordance with the present invention, a visualization surface representative of a portion of the brain of a subject at a selected depth is generated by combining an actual representation of the surface of the head of the subject, which is derived from image data representative of the anatomical configuration of the subject's head, with an idealized representation of the head surface, where the combining eliminates or substantially reduces from the visualization surface any protrusions, concavities or other irregularities and provides for an accurate representation of the E-field that would be induced on the brain portion corresponding to the visualization surface by a TMS coil device used to stimulate the brain of the subject. The contribution of each of the actual and idealized representations of the head surface to the combination is a function of the depth of the visualization surface, and the visualization surface resulting from the combination is scaled in size based on the depth of the visualization surface.

In one embodiment, the visualization surface resulting from the combination is a substantially convex surface. In another embodiment, the idealized representation of the head surface is a function of convex regions of the scalp and the absence or substantial absence of any protrusions, bumps or irregularities in the scalp, which have been removed or substantially reduced. In a further embodiment, the idealized representation of the head surface is an ellipsoid.

In a further embodiment, the visualization surface resulting from the combination is compared with the actual representation of the head surface and, if a differential between the former and latter exceeds a predetermined threshold, a new visualization surface is generated by adjusting the contribution of the actual and idealized representations to the combination as a function of the differential. In one embodiment, the differential is an average of the distances between a plurality of corresponding points defining the actual representation of the head surface and the visualization surface.

BRIEF DESCRIPTION OF THE DRAWINGS

Other objects and advantages of the present invention will be apparent from the following detailed description of the presently preferred embodiments, which description should be considered in conjunction with the accompanying drawings in which like references indicate similar elements and in which.

DETAILED DESCRIPTION OF THE INVENTION

In NBS, MRI image data representative of the configuration of the anatomy of a subject's head, which has been previously collected, is used to generate a three dimensional ("3D") image representative of the head and also visualization surfaces representative of portions of the brain at selected depths below the scalp or head surface. The NBS display typically shows a visualization surface overlaid on a 3D image of the head, the position of a TMS coil device being used to stimulate a target site on a portion of the brain in relation to the head surface and the visualization surface, and the E-field induced in a region of the brain surrounding a stimulated target site on the visualization surface.

Figure 1A:
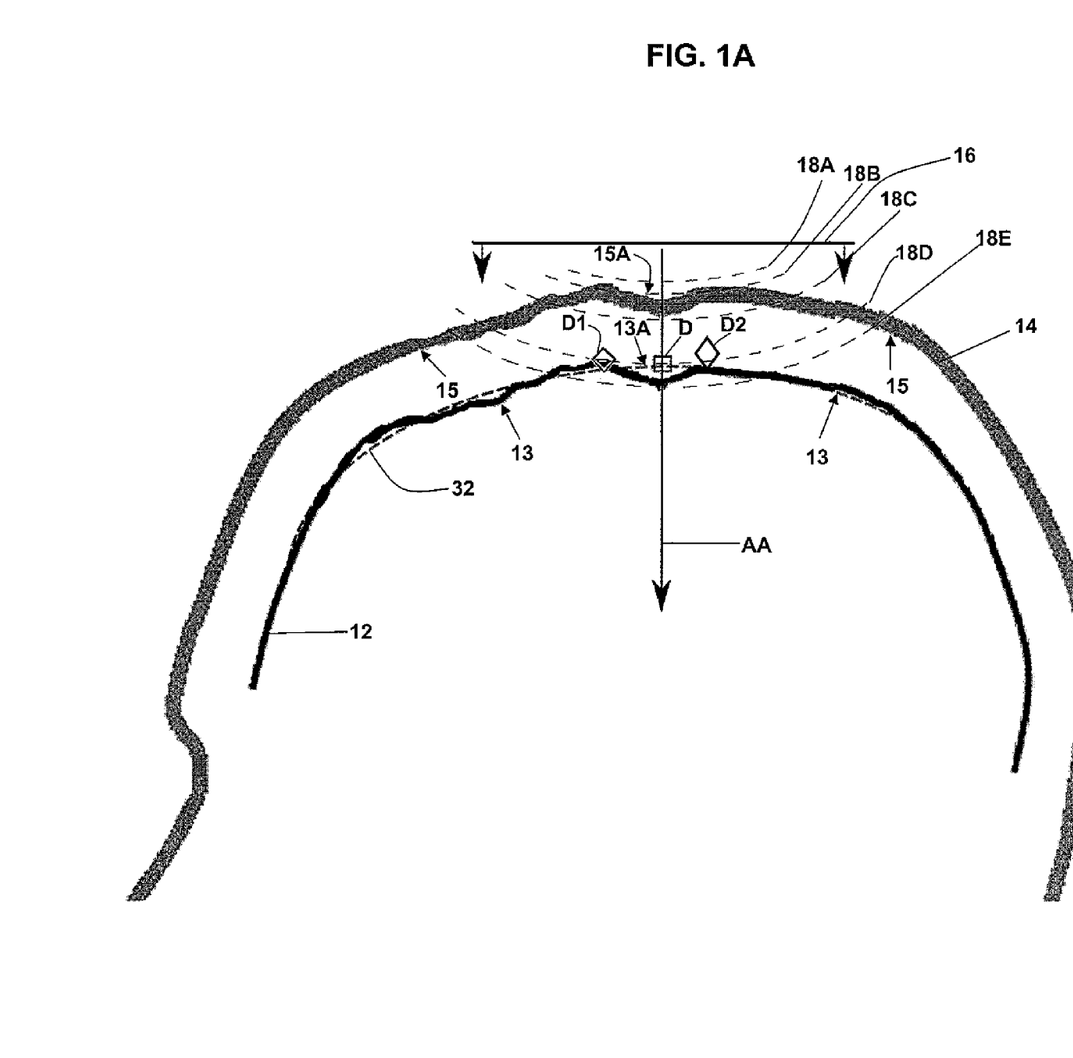
FIG. 1A is a cross-sectional view of a portion of an exemplary head surface of a subject including visualization surfaces corresponding to actual and idealized representations of the head surface and electric field contours induced by a TMS coil device positioned above the head surface.
Figure 2A:
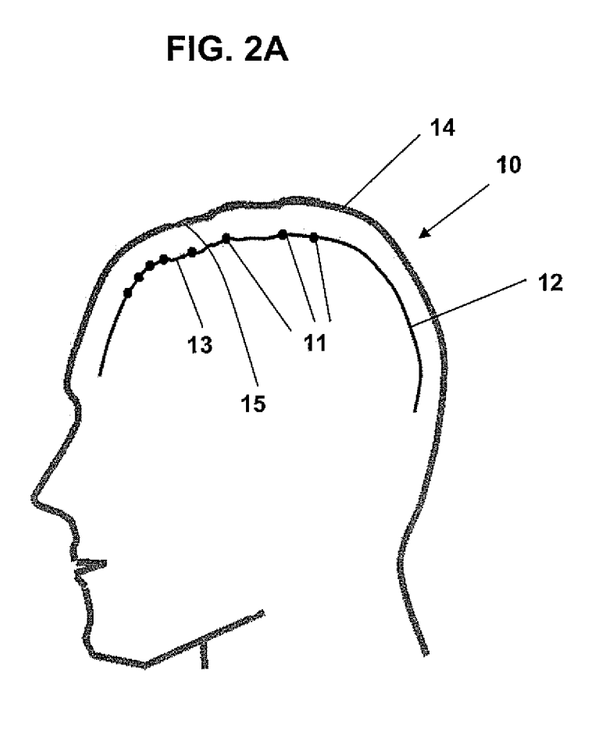
FIG. 2A is a cross-sectional view of the head of the subject of FIG. 1A including the visualization surface corresponding to the actual representation of the head surface.

In prior art NBS, the configuration of the visualization surface which is generated substantially corresponds to the actual configuration of the head surface of the subject. FIG. 1A shows a cross-sectional view of a typical head 10, a visualization surface 12 of a portion of the brain underlying scalp 14 of the head 10 where the visualization surface 12 has been generated in accordance with prior art techniques, a substantially idealized visualization surface 32 of the portion of the brain of the head 10 at the same depth as the surface 12, a TMS coil device 16 positioned above the scalp 14 and contours 18 representing isosurfaces of the E-field induced by the TMS coil device 16 at various depths below the scalp 14. For ease of explanation, the device 16 is shown in FIG. 1A positioned slightly above the scalp 14, although in practice the device 16 ordinarily is placed directly upon the scalp 14. Referring to FIG. 1A, the visualization surface 12 includes bumps, protrusion and irregularities 13 substantially corresponding to the surface shapes, namely, bumps, protrusion and irregularities 15, existing in the scalp 14. Referring to FIG. 2A, which is a view of the head 10 with only the visualization surface 12 shown, the visualization surface 12 includes points 11 representative of the maximum E-field induced on the brain at the depth of the visualization surface 12 that would be displayed on the visualization surface 12, as the TMS coil device 16 is moved along the scalp 14. The visualization surface 12, as typical in the prior art, does not include the points 11 in any concavities 13 in the visualization surface 12 that correspond to the overlying concavities 15 in the scalp 14.

Figure 1B:
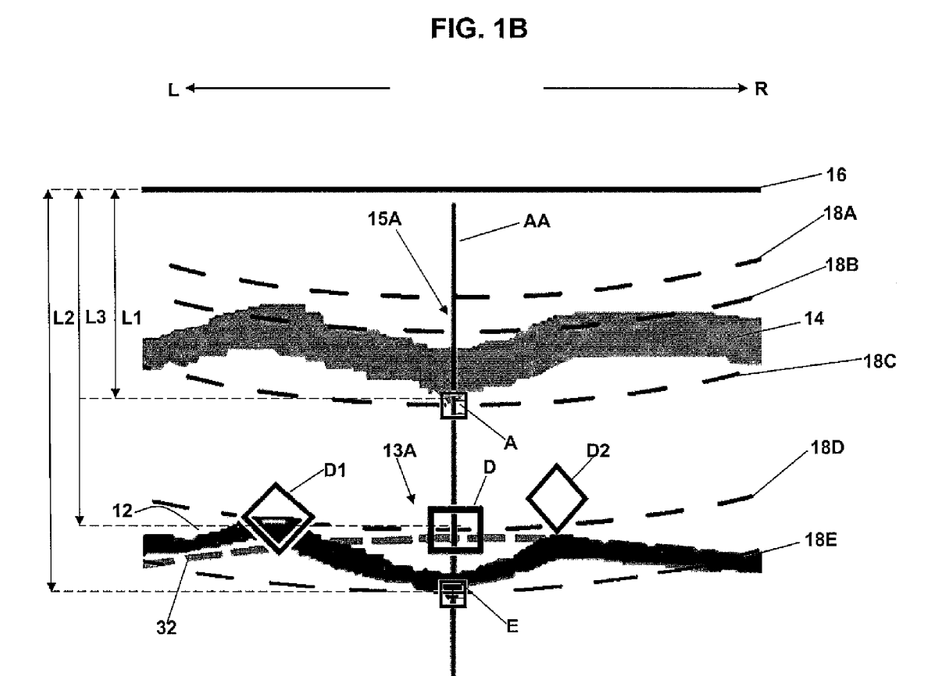
FIG. 1B is a magnified view of a portion of the head surface shown in FIG. 1A.

FIG. 1B is a magnified view of a portion of FIG. 1A where the scalp 14 includes a concavity 15A. Referring to FIGS. 1A and 1B, the E-field induced by the TMS coil device 16 has a maximum at a point on a visualization surface, such as the visualization surface 12, intersecting the contour 18 having the largest E-field value. In the exemplary embodiment of the TMS coil device 16 shown in FIGS. 1A and 1B, the aiming or focusing direction of the TMS coil device 16 corresponds to a line AA extending orthogonally from the TMS coil device 16. The line AA extends through a point A in the concavity 15A and a point E in the concavity 13A on the visualization surface 12, where the point A is on the contour 18C and a distance L1 from the TMS coil device 16 and the point E is on the contour 18E and a distance of L2 from the TMS coil device 16. In addition, only for purposes of illustration, the scalp 14 is treated to have conductive properties similar to the brain, such that when the TMS coil device 16 is positioned as shown, the maximum E-field induced in the scalp 14 is at the point A in the concavity 15A. On the prior art NBS display, the maximum E field induced by the TMS coil 16, which is positioned to stimulate a target site located at the point E in the concavity 13A in the visualization surface 12, would be represented as points D1 and D2 on the visualization surface 12. The points D1 and D2 correspond to points on the contour 18D spaced from the line AA and immediately adjacent to the concavity 13A. Although the point E within the concavity 13A of the visualization surface 12 is the stimulation target, the maximum E-field represented on the visualization surface 12 cannot be at the point E within the concavity 13A because of the shape of the concavity 13A. Also, if the stimulation target site is below the point E, the visualization surface 12 would be at an increased depth within the brain, such that the actual target site of the point E would no longer be on the visualization surface 12. In addition, if the stimulation target site is above the point E, for example, on the idealized surface 32, the actual target site of the point E also would not be on the idealized surface 32, such that the TMS coil device 16 similarly cannot be positioned to stimulate the target site actually at the point E, based on the maximum E-field represented on the idealized surface 32. Thus, by using prior art techniques to represent a surface of the brain at a particular depth, the TMS coil device 16 cannot be positioned to aim at a target site below, above or at the point E due to the shape of the concavity 13A.

As well known, in NBS, it is desirable to identify and know the position of the TMS coil device in relation to the scalp that induces a maximum E-field at a target site on a portion of the brain at a particular depth. Referring to the exemplary head 10 shown in FIGS. 1A and 1B, when the target site on a portion of the brain, which is at a depth corresponding to the depth represented by the visualization surface 12, is aligned with the point A on the scalp 14 of the head 10, the concavity 13A in the visualization surface 12 causes the representation of the maximum E-field to be shown as at the points D1 and D2 on the visualization surface 12. Thus, the position of the TMS coil device 16 in relation to the scalp 14 that would induce a maximum E-field at a target site E on the portion of the brain at the selected depth cannot be determined, because the maximum E-field is shown at the points D1 and D2. In addition, it is likely that, if the TMS coil device 16 is moved slightly along the surface of the scalp 14 in the direction of the arrow R or L, the maximum E-field shown on the visualization surface 12 would remain at or near the points D1 and D2, only the point D1 or only the point D2. Thus, the position of the TMS coil device 16 in relation to the scalp 14 cannot be determined precisely for purposes of stimulating a target site corresponding to a portion of the brain directly underlying the point A on the scalp 14, because the target site on the portion of the brain is aligned with the concavity 15A in the scalp 14. Consequently, the position of the TMS coil device 16 cannot be identified and stored to provide for repeated, precise, maximum stimulation of a target site on the brain aligned with the point A on the scalp 14.

Figure 2B:
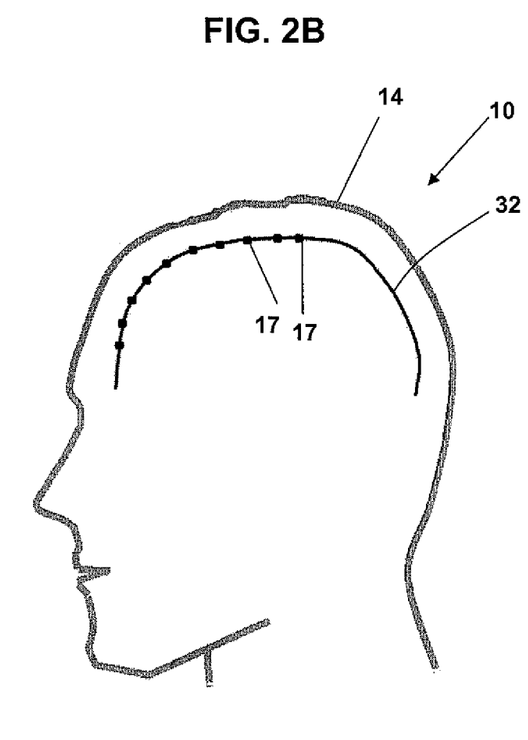
FIG. 2B is a cross-sectional view of the head of the subject of FIG. 1A including the visualization surface corresponding to the idealized representation of the head surface.

Ideally, it is desirable to represent a portion of the brain of a subject, at a selected depth below the scalp, using a smooth or substantially convex-shaped curve, because the position of the TMS coil device, in relation to the head of the subject, that induces a maximum E-field at a target site on the brain then can be precisely identified. Referring to FIGS. 1A and 1B, if the idealized visualization surface 32 were used to represent the portion of the brain at the selected depth, the maximum E-field for the TMS coil device 16 aligned with the point A on the scalp 14 would be represented on the visualization surface 32 only at the point D, which is at the intersection of the line AA and contour 18D and a distance L3 from the TMS coil device 16. Further referring to FIG. 2B, which is a view of the head 10 with only the visualization surface 32 shown, the smooth, convex shape of the surface 32 provides that as the TMS coil device 16 is gradually moved along the scalp 14, such as in the direction of the arrow R or L, points 17 representative of the maximum E-field induced on the surface 32 by the TMS coil device 16 also follow substantially, correspondingly along the surface 32. The visualization surface, however, must still very closely approximate the shape of the brain to provide that the regions neighboring a target site are properly oriented so that the position of a TMS coil device in relation to the head that induces a maximum E-field at a target site can be accurately identified.

In accordance with the present invention, a visualization surface representative of a portion of a brain of a subject at a selected depth is generated to provide that, on a NBS display showing the position of a TMS coil device in relation to the visualization surface and the anatomy of the subject's head, as the TMS coil device is moved gradually across the scalp of the subject, the representation on the visualization surface of a maximum E-field induced at a target site on the brain portion at the selected depth by the TMS coil device correspondingly moves along the visualization surface. Consequently, the position of the TMS device in relation to the subject's head that induces a maximum E-field at a target site on a portion of the brain at the selected depth can be identified to provide for repeated, accurate stimulation of the target site with the TMS coil device.

Figure 3:
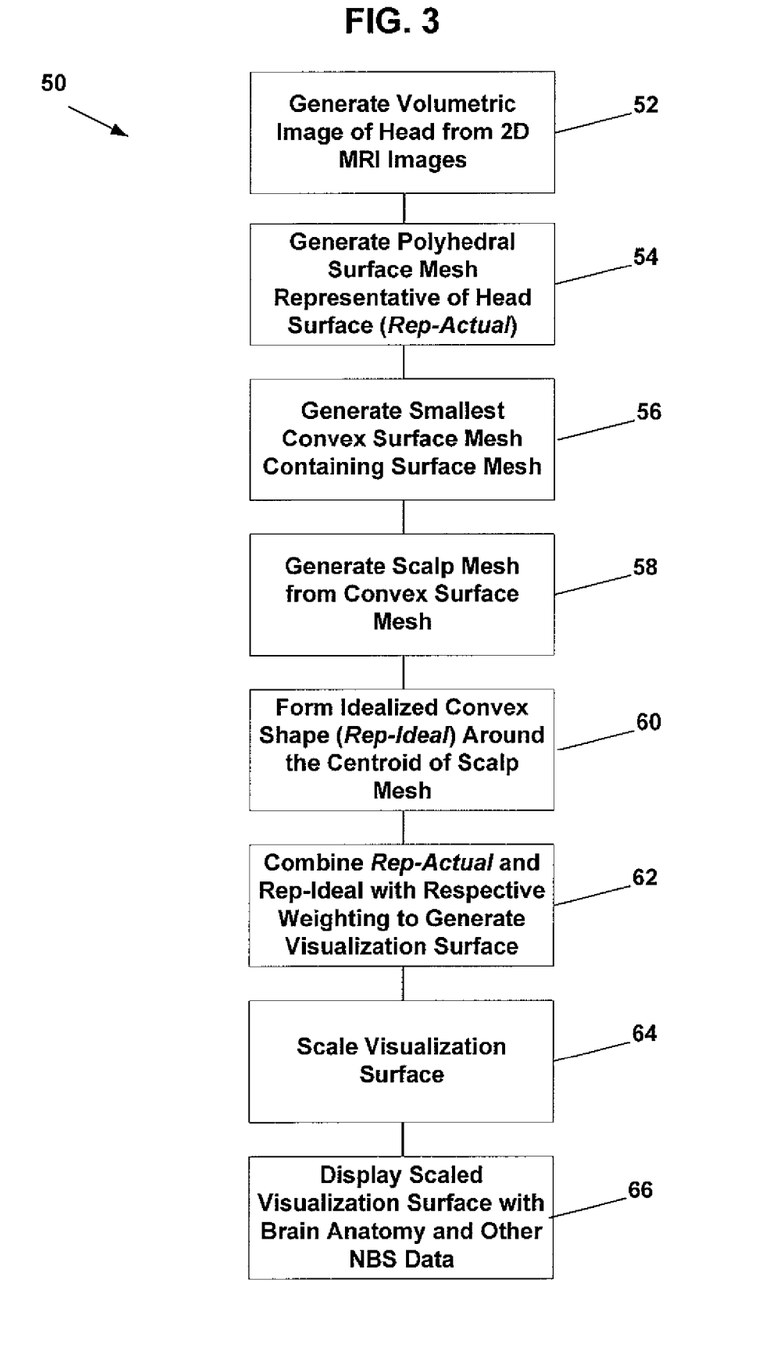
FIG. 3 a flow diagram of an exemplary process for generating a visualization surface at a depth of the brain, in accordance with the present invention.

FIG. 3 shows an exemplary process 50 for generating a substantially convex visualization surface for a plurality of depths of the brain, in accordance with the present invention, which provides that the position of the TMS coil device in relation to the subject's head inducing a maximum E-field at a target site on the brain at a selected depth can be precisely identified. It is to be understood that the data processing steps set forth in the process 50 may be readily performed by a processor having sufficiently high processing power to supply output data on a display in real time or substantially real time and including a memory, and where the processor is coupled to a display, such as a monitor, and a data entry device, such as a mouse and keyboard. The processor is, for example, a microcontroller programmed to perform TMS in connection with a TMS coil device as described, for example, U.S. Pat. No. 6,849,040, assigned to the assignee of this application and incorporated by reference herein. For purposes of highlighting the features of the invention, the process 50 is illustrated in connection with the exemplary head 10 described above. It is also to be understood that, although data computations and processing for individual steps in the exemplary process 50 may be well known or conventional in the art, the combination of steps of the exemplary process 50 is inventive and generates an inventive visualization surface having advantages over prior art visualization surfaces, such as for use in NBS.

Referring to FIG. 3, in step 52 previously collected 2D MRI image data representative of the anatomical configuration of the head 10 is combined and segmented to generate a volumetric image of the head defined by a plurality of voxels, using data processing techniques well known in the art. The coordinates of the voxels defining the head surface or the scalp 14 of the head 10 are identified and then stored in a memory, also as well known in the art.

Figure 4A:
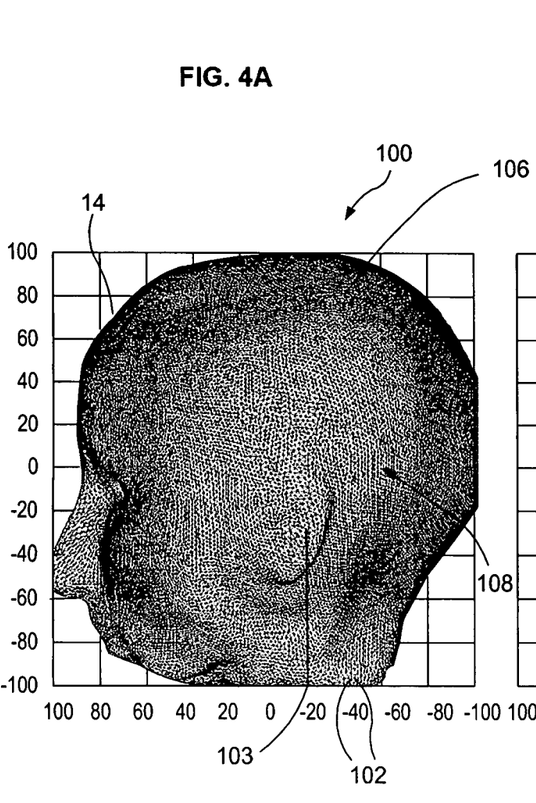
FIG. 4A is an exemplary surface mesh representation of a subject's head.

Then in step 54, a polyhedral surface mesh 100 representative of the surface of the head 10, where the surface mesh 100 is defined by a plurality of polygons 102, is generated, as shown in FIG. 4A, using data processing techniques well known in the art. The typical polygon is a triangle about one to two millimeters long and about one to two millimeters wide. Referring to FIG. 4A, the sizes of the individual polygons 102 are proportional to the sizes of the voxels, such that the surface mesh 100 has substantially the same level of detail (resolution) as the MRI image data. For ease of reference, the surface mesh 100 is referred to below as an actual representation of the head surface 14, or Rep-Actual.

In step 56, the smallest convex surface mesh, or a convex hull, that can contain or envelop the surface mesh 100 is generated, using data processing techniques well known in the art. In addition, a bounding box containing the surface mesh 100 and defining a set of coordinates within which the head 10 is located is generated, also using data processing techniques well known in the art.

Figure 4B:
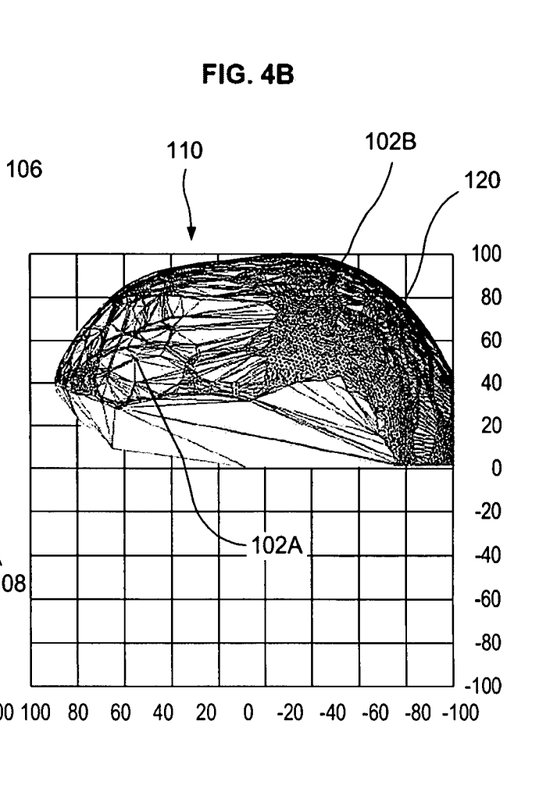
FIG. 4B is an exemplary scalp mesh representation of the head of FIG. 4A, in accordance with the present invention.

In step 58, polygons defining lower parts of the head 10, such as the parts below the ears, are identified, and then a new convex surface mesh with such polygons removed from the convex surface mesh is generated, also using data processing techniques well known in the art. In addition, in the new convex surface mesh, polygons having an area exceeding a predetermined area ("large polygons") and all polygons that share vertices with the large polygons ("neighbor polygons") are identified, and then a resultant convex surface mesh is generated from the new convex surface mesh by removing the large and neighbor polygons, also using data processing techniques well known in the art. The resultant convex surface mesh is a scalp mesh 110, as shown in FIG. 4B.

For a typical head, the removal of the neighbor polygons from the convex surface mesh, as performed in step 58, corresponds to the removal of isolated portions of the convex surface mesh that correspond to convex subregions of the head surrounded by concave regions. Referring to FIGS. 4A and 4B, as a result of geometric properties of the convex surface mesh, and the relatively small size of the polygons 102 in the surface mesh 100, the large polygons of the convex surface mesh correspond to concavities in the surface mesh 100, such as, for example, the concave region between an ear and the skull. Referring to FIG. 4B, the convex surface mesh includes the polygons 102 that form the shape of the skull cap of the head 10 with protrusions and holes removed, where a few polygons 102A populate regions at which the head 10 has bumps and many polygons 102B densely populate other regions of the head 10. Also referring to FIG. 4A, it is seen that the convex subregion above left ear 103 of the head 10 produces many polygons 102 for fitting an idealized representation of a head surface, such as, for example, an ellipsoid, as discussed in detail in step 60 below, to an actual representation of a head surface of a subject, and that irregular subregion 108 above left temple 105 of the head 10 produces only a few polygons.

Referring again to FIG. 3, in step 60, the vertices of all remaining polygons in the scalp mesh 110 are identified and then stored. Based on the vertices of the remaining polygons, an estimate of the centroid μ of the brain of the head is computed, using well known techniques. Then, an idealized convex shape, for example, an ellipsoid, is formed around the centroid and fitted to the extracted vertices of the scalp mesh 110 using the least-squares method. The idealized convex shape fits the convex regions of the scalp 14, and the concavities in the scalp 14 are substantially ignored. In one embodiment, an ellipsoid is a sufficiently ideal convex shape because, if a TMS coil device were positioned on or near the outer surface of an ellipsoid-shaped body having conductive properties such as those existing in the brain, and moved gradually along the outer surface of the ellipsoid body, the E-field induced along the outer surface of the ellipsoid would change correspondingly with movement of the TMS coil device. For ease of reference, the idealized convex shape representation of the head surface generated in step 60 is referred to below as Rep-Ideal.

In a preferred embodiment, in step 60 a bounding box of the topmost part of head 10, or the skull cap of the head 10, is generated, using techniques well known in the art. Based on the contents of the bounding box, an estimate of the centroid μ of the brain is computed. Then, an ellipsoid having its centroid at μ and fit to the vertices of the scalp mesh 110, as generated in step 58, is generated. As discussed above, the vertex density of the scalp mesh 110 is largest on top of the regions of the skull cap that correspond to the most convex regions of the actual head surface, which is represented by the surface mesh 100. Hence, the substantially convex regions of the surface mesh 100 have the largest influence on the shape of the ellipsoid. In a preferred embodiment, the ellipsoid is fit to the vertices of a head surface using the well known technique of minimizing least squares error, such as by taking the pseudoinverse.

In step 62, Rep-Actual and Rep-Ideal are combined to generate a resultant visualization surface V(D) as follows:

$$V(D) = w_{actual} * \text{Rep-Actual} + w_{ideal} * \text{Rep-Ideal} \quad (1)$$

where $w_{actual}$ and $w_{ideal}$ are weighting factors and D is the distance between the scalp 14 and a stimulation target site on a portion of the brain of the head 10 ("depth of the resultant visualization surface" or "peeling depth"). Thus, the resultant visualization surface is a weighted average of the surface mesh 100, in other words, the representation of the actual head surface, and an idealized convex shape representation of the head surface generated from the scalp mesh 110.

In accordance with the present invention, Equation (1) is used to generate a visualization surface of the brain at a particular depth having a configuration beneficial for use in NBS by balancing the following objectives.

1. The shape of the portion of the brain represented by the visualization surface should be anatomically plausible. As a volumetric segmentation of the brain is not conventionally performed, anatomical plausibility is a function of how much the shape of the brain resembles the shape of the scalp or head surface.

2. The shape of the portion of the brain represented by the visualization surface should be sufficiently smooth or convex to provide that the electric field represented on the visualization surface corresponds to actual behavior of the E-field in the brain at the depth of the visualization surface. This second objective apparently contradicts the first objective because, if the brain is a perfect sphere, then the actual representation of the E-field on the visualization surface would be ideal.

As the objectives 1. and 2. are contradictory, in accordance with the present invention, the weightings $w_{actual}$ and $w_{ideal}$ in Equation (1) are a function of D. For increasing D, the influence of the objective 1. decreases and, thus, the weighting on Rep-Actual is decreased, which results in an increase in the weighting on Rep-Ideal. The application of such weightings to Equation (1) for increased peeling depth causes minimal or no error in the configuration of the resultant visualization surface, because, at greater depths within the brain, there do not appear to be any surfaces on the brain that are visible. Therefore, projecting a miniature cortex at greater depths in the brain does not serve any purpose. In contrast, as the peeling depth approaches zero, the weighting on Rep-Ideal does the same and the resultant visualization surface approaches the configuration of Rep-Actual, as per objective (1).

In a preferred embodiment, the weightings $w_{actual}$ and $w_{ideal}$ are determined by a linear function of the peeling depth, and additional constraints are implemented to prevent a weighting from becoming less than zero or more than one, such that $w_{actual} + w_{ideal} = 1$. In another embodiment, Rep-Ideal is generated or modified, as suitable, based on experimental data relating to an idealized convex shape representation of the head surface of the head of another subject.

Referring again to FIG. 3, following step 62, in step 64 V(D) is proportionately scaled in accordance with the peeling depth D.

In a preferred embodiment of steps 62 and step 64, a user selects the peeling depth D and an axial depth AD. The axial depth AD determines the portion of the head, such as the jaw, neck, etc., excluded from the generation of the scalp mesh 110. As discussed above, the peeling depth determines the parameterized shape (step 62) and the scaling (step 64) of the visualization surface generated to represent a portion of the brain at the depth D. The axial depth sets forth the axial range [0, AD] in which the head surface 14 is made transparent for purposes of display of the visualization surface on a NBS display. In one embodiment, the peeling depth represents a percentage p from 0% to 50%, and the axial depth AD is between about 0 mm to 250 mm. For example, if p=20% and AD=50 mm, then the volume of the model of the brain that is generated is approximately 80% of the actual volume of the head, and the head surface 14 is made transparent downwards from a point 50 mm from the top of the head 10. Thus, if the peeling depth D is selected so that p is close to the maximum 50%, then referring to Equation (1), $w_{actual}$ is close to zero and $w_{ideal}$ is close to one. In one embodiment, the scale of p is such that p is about equivalent to millimeters if the head model represents an adult male head. For example, on top of the head, a p of 20% is equivalent to about 20 mm measured from the brain to the nearest surface point on the scalp 14.

In an exemplary embodiment of step 62, when peeling depth p is between minimum and maximum values, the weightings $w_{actual}$ and $w_{ideal}$ are determined by a linear model where $$w_{actual} = f_0 * \text{scale} + f_1 \quad (2)$$

where scale=1−p, in other words, when peeling depth p is 0.1 (10%), scale is 0.9 (90%), such that the visualization surface needs to be reduced in size to 90% of the original scalp size. As $w_{actual} + w_{ideal} = 1$, then $$w_{ideal} = 1 - f_0 * \text{scale} - f_1 \quad (3)$$

If $p_{min}$ and $p_{max}$ correspond to the minimum and maximum peeling depths, for example, 0% and 50%, then the parameters $f_0$ and $f_1$ are readily determined by rewriting the constraints for Equation (1) as follows.

$$f_0 * (1 - p_{min}) + f_1 = 1 \quad (4)$$

and $$f_0 * (1 - p_{max}) + f_1 = 0 \quad (5).$$

By substituting the values of $p_{min}$ and $p_{max}$, Equations (4) and (5) are readily solved to find that $f_0 = 2$ and $f_1 = -1$. The value of p selected by the user can then be used to calculate scale, $w_{actual}$ and $w_{ideal}$ using the known values for $f_0$ and $f_1$.

Following the computation of $w_{actual}$ and $w_{ideal}$, the shapes represented by Rep-Actual and Rep-Ideal are combined using the weightings $w_{actual}$ and $w_{ideal}$ in accordance with Equation (1) by representing each of the shapes as a finite set of points or an equation. In a preferred embodiment, the representation of the shapes is a finite set of points when the equivalent equation becomes too complex. For example, it is very difficult to represent the shape of an ear accurately using an equation.

In an exemplary embodiment, Rep-Actual is represented by a set of points and Rep-Ideal, which is an ellipsoid, is represented by an equation. In addition, the visualization surface resultant from the combination as per Equation (1) is represented by a set of points, where the number of points equals the number of points on the surface mesh 100. The set of points corresponds to vectors $V_i$, each of which contains the coordinates of a scalp point i and where the origin of the coordinate system is the centroid µ calculated for the ellipsoid Rep-ideal. If $l_i$ is a line intersecting both µ and $V_i$, then line $l_i$ intersects the ellipsoid at two points. Further, if $e_i$ is the intersection point closest to $V_i$, then $e_i$ corresponds to $V_i$ in the sense that $e_i$ is the projection of $V_i$ on the ellipsoid Rep-Ideal. Thus, the combining of the shapes is performed by combining corresponding points, in other words, scalp points and their projections. Based on a pair ($V_i$, $e_i$), a new point $b_i$ for modeling the surface of the brain is computed. The corresponding points are combined as follows $$b_i = w_{actual} * V_i + w_{ideal} * e_i \tag{6}$$

and the computation of Equation (6) is repeated for each i to obtain a set of points corresponding to a model of a portion of the brain, in other words, the visualization surface at the peeling depth D. The brain model, at this stage of the data processing, is approximately the same size as the scalp mesh model of the brain, as the points $e_i$ are on the surface of the ellipsoid that is the idealized representation of the scalp. Then, per step 64, each of the points $b_i$ is scaled, in other words, moved closer to µ based on the peeling depth. As the origin is at µ, each of the points $b_i$ is $b_i$*scale.

In another embodiment, Rep-Ideal is formed from a plurality of idealized convex shapes Rep-Ideal$_n$, each of which is formed around the centroid p of the brain determined from, and fitted to the convex regions of, the scalp mesh. The use of a plurality of, preferably complex, shapes for forming Rep-Ideal is advantageous and desirable for NBS, where the objective of a TMS procedure is to stimulate brain regions far from the motor cortex. In such embodiment, a plurality of idealized representations of the head surface, for example, two ellipsoids, form Rep-ideal, such that there are M projections proj where $$b_i = \Sigma_{j=1}^M proj_j(V_i) * w_j \tag{7}$$

and $$\Sigma_{j=1}^M w_j = 1 \tag{8}$$

and three weights $w_1$, $w_2$ and $w_3$; where weight $w_1$ equals $w_{actual}$, $w_2$ is the weight of a first ellipsoid $w_{ideal1}$ and $w_3$ is the weight of a second ellipsoid $w_{ideal2}$. The projection $proj_1$ is $proj_1(V_i) = V_i$ and the projections $proj_2$ and $proj_3$ are simple projections of scalp points on the two ellipsoids, where $proj_2(V_i) = e_i$. $w_2$ and $w_3$ are set to zero depending on $V_i$ as follows. When $V_i$ is close to the motor cortex of the brain, $w_3$ is set to zero. Based on normalization, $w_2 = w_{ideal1}$, such that $b_i$ is exactly the same as if only a single ellipsoid is used to form Rep-Ideal. In contrast, when $V_i$ is far from the motor cortex, $w_2$ is set to zero and $w_3 = w_{ideal1}$, such that $b_1$ is calculated based on the second ellipsoid.

Figure 5:
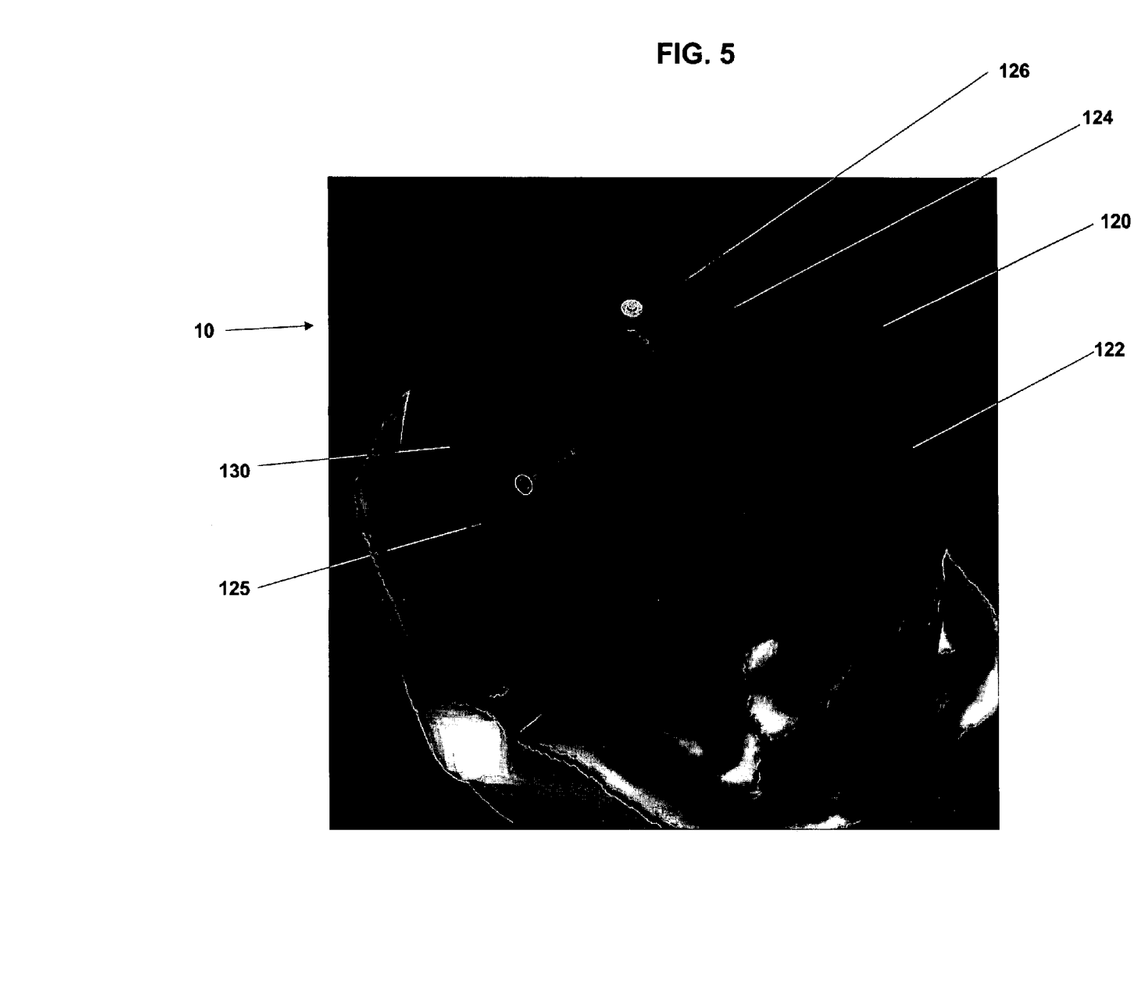
FIG. 5 is a perspective view of a three dimensional representation of an exemplary head on which is overlaid a visualization surface of the brain, in accordance with the present invention, and showing the E-field induced by a TMS coil device on the visualization surface.

Referring again to FIG. 3, following step 64, in step 66, based on the position of the TMS coil device 16 in relation to the scalp 14, the E-field induced on the visualization surface V(D) at a user selected peeling depth is computed. A 3D image of the brain anatomy overlaid by the visualization surface including the E-field induced by the TMS coil device is then displayed, for example, on a monitor associated with performing NBS, as shown in FIG. 5. In a preferred embodiment, the maximum E-field at the target site, along with the E-field in the region surrounding the target site, is indicated on the visualization surface. Referring to FIG. 5, the E-field 120 is shown overlaid upon an image of the brain anatomy 122 of the head 10. In a preferred implementation on a display, the E-field 120 is shown in color overlaid on the anatomy 122 shown in grayscale, thus allowing the user to easily distinguish the two types of information. Dark spot 124 below white cylinder 126 represents large values of the E-field, which are preferably shown in dark red, while dark regions 125 near boundary 130 of the E-field 120 circle, which preferably are shown in dark blue, represent the minima of the E-field.

In one embodiment of the present invention, the inner surface of the skull, instead of the outer surface of the scalp, is used to generate Rep-Actual, for example, when the external shape of a head does not sufficiently accurately follow the shape of the cranial cavity.

In another embodiment, Rep-Actual is generated based on the actual form of the brain or the cortex, as determined by segmentation of the MRI images. By use of such Rep-Actual, the visualization surface generated by Equation (1) may have increased anatomical fidelity while also exhibiting irregularities in the representation of the induced E-field on the visualization surface.

In a further embodiment, a user may select one of several additional constraints to be applied to Equation (1) for generating a visualization surface. The constraints, for example, correspond to and are based upon experimental results obtained from generating visualization surfaces for other heads having a head surface configuration found to be similar to the configuration of a subject head, and are selected to avoid generating a visualization surface where the user would have difficulty interpreting the E-field information indicated on the visualization surface.

In a further embodiment, Rep-Ideal is derived using one or more selected optimization criteria and constraints dependent upon the current position of the TMS coil device. The optimization criteria and constraints may include, for example, that a visualization surface is generated only at a local region near a target site for stimulation which is known in advance. For example, if in the MRI image data representative of the head, the data representative of the right hemisphere of the brain is incomplete and the data representative of the left hemisphere of the brain is complete and intact, and further if a predetermined stimulation target site of interest is in the left hemisphere, only the portions of the surface mesh 100 close to the predetermined site are used to fit a curved surface at the desired depth. The portions of the surface mesh 100 far from the stimulation site are ignored in the fitting of the curved surface.

In another embodiment, a microcontroller for performing NBS, and also capable of generating a visualization surface in accordance with the present invention, uses information representative of the position of the TMS coil device in relation to the head and the E-field induced on the visualization surface to automatically control, or provide control information to the user for controlling, the position or orientation of the TMS coil device in relation to the head, such that when the TMS is moved along the surface of the head, the amplitude of the induced E field on the visualization surface remains constant. A constant amplitude E-field, for example, can be defined by a user. Such controlled application of E-field is of particular use, for example, where the amplitude of the maximum E-field depends on the position or orientation of the TMS coil device in relation to the scalp, and it is desirable to stimulate a target region of the cortex with the TMS coil device in a uniform manner.

In a further embodiment, referring again to FIG. 3, after step 64, the coordinates of the visualization surface are compared to corresponding coordinates of Rep-Actual to determine if the difference between the shape of the visualization surface and the shape of Rep-Actual is within a predetermined threshold. If yes, then step 66 is performed. If no, new values for $w_{actual}$ and $w_{ideal}$ are assigned or computed, preferably as a function of the difference, and step 62 is performed again to generate a visualization surface. In a preferred embodiment, the difference is an average of the distances between a plurality of corresponding coordinates of Rep-Actual and the visualization surface.

In a further embodiment, in the event an idealized representation of the head surface of a head is determined to be unsuitable for the subject head, an alternatively shaped idealized representation, such as an alternatively shaped ellipsoid, may be used as Rep-ideal.

Although preferred embodiments of the present invention have been described and illustrated, it will be apparent to those skilled in the art that various modifications may be made without departing from the principles of the invention.

What is claimed is:

1. An apparatus for generating a representation of a portion of a brain for use in transcranial magnetic stimulation ("TMS") comprising:
    a non-transitory computer readable medium having a process encoded thereon including the steps of:
   generating an actual representation of a head surface of a head,
   generating an idealized representation of the head surface,
   weighting the actual and idealized representations with first and second weightings, respectively, wherein the first and second weightings are a function of a depth beneath the head surface,
   combining the weighted actual and weighted idealized representations to form an unscaled visualization surface,
   wherein the visualization surface is representative of a portion of the brain within the head at the depth,
   scaling the unscaled visualization surface based on the depth to generate the visualization surface, and
   providing for display of the visualization surface, and
   a processor configured to perform said process stored on said computer readable medium.

2. The apparatus of claim 1, wherein the non-transitory computer readable medium further comprises process steps encoded thereon including:
    computing, based on the visualization surface, an electric field ("E-field") induced by a TMS induction coil device on a portion of the brain at the depth; and
    providing for display of the induced E-field on the visualization surface.

3. The apparatus of claim 2, wherein the non-transitory computer readable medium further comprises process steps encoded thereon including:
    providing for display of the TMS coil device positioned in relation to the visualization surface, a representation of the head surface corresponding to the actual representation of the head surface and a volumetric representation of the head.

4. The apparatus of claim 3, wherein the non-transitory computer readable medium further comprises process steps encoded thereon including:
    generating information representative of the position of the TMS coil device in relation to the head surface for a target site on the visualization surface stimulated by the TMS coil device.

5. The apparatus of claim 4, wherein the non-transitory computer readable medium further comprises process steps encoded thereon including:
    providing or automatically storing the position of the TMS coil device after performing the step of:
    identifying a single maximum E-field on the visualization surface for the target site.

6. The apparatus of claim 2, wherein the non-transitory computer readable medium further comprises process steps encoded thereon including:
    providing for display of a maximum and a minimum of the induced E-field on the visualization surface.

7. The apparatus of claim 1, wherein the non-transitory computer readable medium further comprises process steps encoded thereon including:
    wherein the first and second weightings are determined by a linear function of the depth, wherein the sum of the first and second weightings equals one and each of the first and second weightings is not less than zero or more than one.

8. The apparatus of claim 7, wherein the non-transitory computer readable medium further comprises process steps encoded thereon including:
    wherein the first weighting decreases as the depth increases and the second weighting decreases as the depth decreases.

9. The apparatus of claim 1, wherein the idealized representation is an ellipsoid.

10. The apparatus of claim 1, wherein the visualization surface is a substantially convex surface.

11. The apparatus of claim 1, wherein the non-transitory computer readable medium further comprises process steps encoded thereon including:
    wherein the actual representation is a polyhedral surface mesh defined by a plurality of polygons and generated from a volumetric image of the head, the process further comprising:
    generating a smallest convex surface mesh containing the surface mesh defined by a plurality of polygons;
    eliminating polygons of the plurality of polygons, from the smallest convex surface mesh, corresponding to a lower portion of the head, polygons of the plurality of polygons having an area exceeding an area of predetermined large polygons and polygons of the plurality of polygons sharing vertices with the polygons having an area exceeding the area of predetermined large polygons, to generate a scalp mesh; and
    generating the idealized representation based on the scalp mesh.

12. The apparatus of claim 11, wherein the non-transitory computer readable medium further comprises process steps encoded thereon including:
    wherein the generating of the idealized representation based on the scalp mesh further comprises:
    computing a centroid of the brain based on vertices of all polygons in the scalp mesh, wherein the idealized representation is formed around the centroid and fitted to the vertices.

13. The apparatus of claim 12, wherein the idealized representation is an ellipsoid.

14. The apparatus of claim 1, wherein the idealized representation is formed from a plurality of idealized representations.

15. The apparatus of claim 1, wherein the idealized representation is formed from a plurality of n idealized representations idealized$_n$, wherein each of the idealized$_n$ representations has a weighting $W_{ideal-n}$ which is a function of a position of a projection of a vector V from a point on a surface mesh onto the corresponding idealized$_n$ representation, in relation to a predetermined portion of the brain.

16. The apparatus of claim 1, wherein the actual representation is derived from magnetic resonance imaging data representative of an anatomical configuration of the head.

17. The apparatus of claim 1, wherein the non-transitory computer readable medium further comprises process steps encoded thereon including:
- comparing the visualization surface with the actual representation of the head surface;
- computing a differential between the visualization surface and the actual representation based on the comparing; and
- generating a new visualization surface by combining the actual and idealized representations with an adjustment, if the differential exceeds a predetermined threshold.

18. The apparatus of claim 17, wherein the adjustment is a function of the differential.

19. The apparatus of claim 1, wherein the combining is a function of at least one optimization criteria and a constraint.

20. The apparatus of claim 19, wherein the constraint is a function of an area of interest in the brain and quality of image data representative of the head for the area of interest in the brain.

21. The apparatus of claim 1, wherein the processor generates control information for controlling position and orientation of a TMS coil device in relation to the head, based on an actual position of the TMS coil device in relation to the head surface and a computation of an electric field induced on the visualization surface, to maintain a constant amplitude electric field induced on the visualization surface.

* * * * *